United States Patent [19]

Nelson

[11] 4,038,417

[45] July 26, 1977

[54] METHOD FOR TREATMENT OF PSORIASIS

[75] Inventor: Eric Loren Nelson, Santa Ana, Calif.

[73] Assignee: Nelson Research & Development Company, Irvine, Calif.

[21] Appl. No.: 588,233

[22] Filed: June 19, 1975

[51] Int. Cl.$^2$ .......................................... A61K 31/135
[52] U.S. Cl. ..................................... 424/330; 424/168
[58] Field of Search ......................................... 424/330

[56] References Cited

U.S. PATENT DOCUMENTS

| 3,276,875 | 10/1966 | Schwalenstocker | 96/109 X |
| 3,885,047 | 5/1975 | Seidehamel et al. | 424/330 |

FOREIGN PATENT DOCUMENTS

| 2,001,768 | 10/1969 | France | 424/274 |

OTHER PUBLICATIONS

Chem. Abs. 1971, vol. 75, p. 109261k (equiv. to S. African Pat. 6905,393).
Chem. Abs., 1968, vol 68, p. 118144.
Chem. Abs. 1975, vol. 75, p. 143994, Jiro et al.
Temime, vol. 71, 1969, p. 42289, Chem. Abs.
Dawson, Chem. Abs., 1970, vol. 72, p. 136423.
Glasser, Chem. Abs., 1967, vol. 66, p. 108258s.
Hospital Formulary, 1966, pp. 1 to 25, Section 4:00 – Antihistamines.

*Primary Examiner*—Dale R. Ore
*Attorney, Agent, or Firm*—Martin A. Voet

[57] ABSTRACT

A composition and method for treating psoriasis in humans comprising the administration to a human suffering from psoriasis of a beta-adrenergic receptor stimulating compound such as isoproterenol.

6 Claims, No Drawings

METHOD FOR TREATMENT OF PSORIASIS

BACKGROUND OF THE INVENTION

1. Field of the Invention

The present invention relates to the therapeutic use of beta-adrenergic receptor stimulating compounds. More particularly, the present invention relates to the use of certain beta-adrenergic receptor stimulating compounds in the treatment of skin conditions such as psoriasis.

2. Background of the Prior Art

Compounds which act on adrenergic receptors are generally classified into two types, namely, compounds which act on alpha receptors and compounds which act on bata receptors. Compounds which act on alpha receptors are generally excitatory and compounds which act on beta receptors are generally inhibitory. For example, norepinephrine is a classic alpha-adrenergic receptor stimulator while isoproterenol is a classic beta-adrenergic receptor stimulator. Compounds which act on adrenergic receptors may have activity on both alpha and beta receptors. However, pure beta adrenergic receptor stimulating compounds such as isoproterenol have essentially no alpha adrenergic receptors stimulating activity.

Psoriasis is a common, chronic, relapsing disease of unknown etiology which consists of elevated, silvery, dry lesions which are known as plaques. Pathologically, there are three obvious changes associated with the disease: (1) increase in the rate of cell division of the epidermis, (2) striking increase in the thickness of the cornified epithelium, and (3) proliferation of the subepithelial capillaries.

Current therapy consists mostly of topical agents containing coal tars and steroids. Ultraviolet irradiation is used. Occasionally, psoriasis is such a serious problem that systemic antimetabolites are employed to help control the epithelial proliferation, e.g. U.S. Pat. No. 3,749,784.

SUMMARY OF THE INVENTION

There has now been discovered a method for treating psoriasis, that is, a method for temporarily alleviating some or all of the signs or symptoms of psoriasis comprising the administration to a human suffering from psoriasis of an effective dose for treating psoriasis of a beta adrenergic receptor stimulating compound such as, for example, isoproterenol. The invention further relates to a composition comprising an effective dose for treating psoriasis of a beta adrenergic receptor stimulating compound together with a topical pharmaceutical carrier and preferably a topical pharmaceutical carrier which is highly skin penetrating.

DETAILED DESCRIPTION OF THE INVENTION

Active compounds which may be used in this invention in the treatment of psoriasis include isoproterenol, its pharmaceutically acceptable salts, e.g., isoproterenol hydrochloride, isoproterenol sulfate, etc., its pharmaceutically acceptable esters, e.g., dipivalyl isoproterenol; and other sympathomimetic amines having primarily beta adrenergic receptor stimulating activity (as opposed to primarily alpha adrenergic receptor stimulating activity), such as, for example, isoetharine, protochyol, albuterenol, chlorprenaline hydrochloride, cyoterenol, deterenol hydrochloride, fenterenol, metaproterenol sulfate, quinterenol sulfate, rimiterol HBr, soterenol, terbutaline sulfate, cinnamedrine, isoxuprine HCl, nylidrin HCl, bamethan sulfate, mesuprine HCl, prenylamine and ritodrine HCl.

Preferred compounds include isoproterenol and its pharmaceutically acceptable salts and esters.

The amount of beta adrenergic receptor stimulating compound which may be used in the method of the present invention is that amount of compound which is an effective dose for the treatment of psoriasis. More particularly, concentrations in the range of about 0.1 to about 10 and preferably about 0.5 to about 5 percent by weight may be used.

The preferred manner of administration is topical, that is, local application including intralesional injection. A typical ointment for topical use contains the following ingredients per gram of ointment.

|  | Mg |
|---|---|
| Active compound. e.g. isoproterenol | 5 |
| Isopropyl myristate | 30 |
| Polawax | 130 |
| Mineral oil | 130 |
| Sodium phosphate dibasic | 4 |
| Sodium phosphate monobasic | 6 |
| Purified water q.s. ad. | 1000 |

Other conventional topical formulations may also be used. That is, the Polawax, a non-ionic emulsifying wax, may be replaced by fatty alcohols, glycol ethers of fatty acids, glycol esters of fatty acids, other wax-like emulsifiers or self-emulsifying fatty alcohol blends. The isopropyl myristate, which is used as an emollient, may be replaced with other isopropyl esters of fatty acids, butyl esters of fatty acids, glycerin, propylene glycol, alcohols, propylene glycol carbonate and other carboxylic acid esters. The mineral oil, which is used to provide an oil phase, may be replaced by petroleum oil, oil extracts from animal sources, e.g. shark oil, lanolin and oil extracts from vegetable sources, e.g. peanut oil. The formulation may also include stabilizers including, for example, EDTA, 8-OH quinoline and conventional antioxidants and preservatives. The formulation may also include agents, such as urea, to improve the hydration of the skin in order to enhance "cosmetic feel" and adsorption of the active compound.

A typical solution for topical use contains the following ingredients per gram:

|  | Mg |
|---|---|
| Active compound e.g. isoproterenol | 5 |
| Purified water | 100 |
| Glycerin (U.S.P.) | 890 |

In addition to the foregoing conventional formulations, the antipsoriatic activity of the active compound described herein may be substantially enhanced by the use of skin penetrating vehicles, i.e., compounds which enhance percutaneous adsorption of the active compound through the skin. Vehicles which enhance the skin penetration of the active compounds disclosed herein include dimethylsulfoxide (DMSO), N-alkyl substituted 2-pyrrolidones e.g., N-methyl-2-pyrrolidone, 2-pyrrolidone and mixtures thereof, dimethylformamide, dimethylacetamide, etc.

2-Pyrrolidone and N-lower alkyl-2-pyrrolidones are available commercially and are made by a number of methods known to those of skill in the art as exemplified by U.S. Pat. Nos. 2,555,353 and 2,267,757. N-lower alkyl-2-pyrrolidones include the straight and branch chain lower alkyl groups having 1-4 carbon atoms. N-methyl-2-pyrrolidone is preferred.

The amount of 2-pyrrolidone or N-lower alkyl-2-pyrrolidone which may be used in the present invention ranges from about 5 to about 99.99 percent and preferably 10-40 percent by weight of the composition.

In carrying out the novel method employing the topical route, the active ingredient formulated as an ointment or solution, as indicated above, is applied to a psoriatic lesion at a rate varying from 0.2 mg. square cm. of skin surface per day up to 10 mg. per square cm. of skin surface per day until the appearance of the psoriatic skin has returned to normal. The ointment or solution is generally applied for five days, preferably using a continuous occlusive dressing. The concentration of active ingredient can vary from about 0.1% to about 10% by weight. With the foregoing concentration, a dose of 0.2 ml per square cm. of skin surface readily supplies the amount of active ingredient specified above.

To illustrate the manner in which the invention is made, the following examples are given. It is understood, however, that the examples are for purposes of illustration and the invention is not to be regarded as limited to any of the specific materials or conditions therein.

EXAMPLE I

The formulations shown below were prepared and tested in an animal model for psoriasis in a double blind basis.

| Ingredients | Formulation Wt. (grams) | |
|---|---|---|
|  | 1 | 2 |
| Isoproterenol | 0.5 | — |
| Water | 31.0 | 30.5 |
| 2-pyrrolidone | 14.0 | 14.0 |
| N-methyl-2-pyrrolidone | 21.0 | 21.0 |
| Cream base | 34.0 | 34.0 |

The animal model used was a hairless mouse screening model. The model utilizes a determination of the reduction of the mitotic index and the inhibition of DNA synthesis as shown by a decrease in the incorporation of radioactive thymidine into DNA.

Crude cell lysate from hairless mouse epidermis labeled with tritiated thymidine was loaded onto a column containing hydroxyapatite, [$CA_{10}$ $(PO_4)_6$ $(OH)_2$] which has a unique property of high affinity for native double stranded DNA but not RNA and proteins. The RNA and proteins was washed through the column with a low salt buffer whilst the DNA remains bound until eluted with a high salt buffer. The absorbance of the DNA at 260 nm was measured in a spectrophotometer from which the amount of DNA per ml of sample may be calculated and then the radioactivity of the DNA was determined. If a drug has been previously given to the animal it may be assumed to have antimetabolic properties in the epidermis if the specific activity of the DNA is significantly decreased.

Utilizing the foregoing animal model, it was found that formulation 1 significantly inhibited DNA synthesis while formulation 2 (placebo) did not inhibit DNA synthesis.

EXAMPLE II 3 patients suffering from psoriasis were treated topically for psoriasis with formulation 1 shown in EXAMPLE I.

In carrying out the treatment, selected, isolated, psoriatic plaques on each of the patients were treated topically twice daily with the above formulation for 2 weeks. Within 10-14 days, the treated plaques on all three patients were resolved, i.e., the plaques disappeared.

I claim:

1. A method for treating psoriasis in humans comprising administering to a human suffering from psoriasis an effective dose for treating psoriasis of a composition comprising isoproterenol or a pharmaceutically acceptable salt thereof, and a pharmaceutical carrier.

2. The method of claim 1 wherein the composition is administered topically to a psoriatic lesion.

3. The method of claim 1 wherein the composition is administered to the psoriatic lesions intralesionally.

4. The method of claim 1 wherein the compound is isoproterenol hydrochloride.

5. The method of claim 1 wherein the compound is isoproterenol sulfate.

6. The method of claim 1 wherein the carrier includes an agent selected from the group consisting of dimethylsulfoxide, 2-pyrrolidone, lower-alkyl-substituted-2-pyrrolidone and mixtures thereof.

* * * * *